United States Patent
Rampf et al.

(10) Patent No.: US 7,230,136 B2
(45) Date of Patent: Jun. 12, 2007

(54) PROCESS FOR PREPARING TERTIARY PHOSPHINES

(75) Inventors: Florian Rampf, Köln (DE); Hans-Christian Militzer, Odenthal (DE)

(73) Assignee: LANXESS Deutschland GmbH, Leverkusen (DE)

( * ) Notice: Subject to any disclaimer, the term of this patent is extended or adjusted under 35 U.S.C. 154(b) by 0 days.

(21) Appl. No.: 10/417,989

(22) Filed: Apr. 17, 2003

(65) Prior Publication Data

US 2003/0229240 A1   Dec. 11, 2003

(30) Foreign Application Priority Data

Apr. 19, 2002   (DE) ................. 102 17 517
May 17, 2002   (DE) ................. 102 22 033

(51) Int. Cl.
*C07F 9/50*   (2006.01)
*C07F 9/28*   (2006.01)

(52) U.S. Cl. ............. 568/8; 568/9; 568/11; 568/16; 568/17

(58) Field of Classification Search ............ 568/8, 568/9, 11, 16, 17
See application file for complete search history.

(56) References Cited

U.S. PATENT DOCUMENTS

| | | | |
|---|---|---|---|
| 2,913,498 A * | 11/1959 | Ramsden ................ | 568/17 |
| 3,499,039 A | 3/1970 | Lorenz et al. ........... | 260/606.5 |
| 4,668,823 A | 5/1987 | Murray .................. | 567/424 |
| 5,621,129 A * | 4/1997 | Hayashi et al. .......... | 556/21 |
| 5,808,163 A * | 9/1998 | Millauer et al. ......... | 568/17 |
| 6,335,471 B1 | 1/2002 | Eastham et al. .......... | 568/17 |

OTHER PUBLICATIONS

Hoffmann, Schellenbeck, Chemische Berichte, 1967, 100 (2), 692-693.
Hoffmann, Schellenbeck, Chemische Berichte, 1966, 99, 1134-1142.
Issleib, Brack; Zeitschr. allg. anorg. Chem. 1954, 277, 258-270.
Adv. Synth. Catal., (month unavailable) 2001, 343 (8), 789-794, Kaye et al "The Use of Catalytic Amounts of CuCl and Other Improvements in the Benzyne Route to Biphenyl-Based Phosphine Ligands".
J. Am. Chem. Soc., (month unavailable) 2001, 123 (11), 2677-2678, Stambuli et al., "Screening of Homogeneous Catalysts by Fluorescence Resonance Energy Transfer. Identification of Catalysts for Room-Temperature Heck Reactions".
Tomori, H. et al: "An Improved Synthesis11-19,21, of Functionalized Biphenyl-Based Phosphine 23 Ligands" Journal of Organic Chemistry (2000), 65(17), 5334-5341, 2000, XPO02248873 * Tabelle 1 *.
Kaye, S. et al: "The use of catalytic amounts of CuCl and other improvements in the benzyne route to biphenyl-based phosphine ligands" Advanced Synthesis & Catalysis (2001), 343(8), 789-794, 2001, XPOOI161250 *das ganze Dokument *.
Schmidbauer H. et al.: "Extreme sterische Hinderung: Synthese und Strunktur des Tetra (tert-butyl) phosphonium Kations—ein Fall von T-Symmetrie" Chemische Berichte., Bd. 113, Nr. 4, 1980, Seiten 1612-1622, XPO02248874 Verlag Chemie GMBH. Weinheim., DE ISSN: 0009-2940 *Seite 1613, unten; Seite 1614, Verbindung 5*.
Dumont W.W. et al.: "IIZinn(II)-halogenidKomplexe mit Tri-tert-butylphosphin und Tris(dimethylamino)phosphin Zeitschrift fur Anorganische und Allgemeine Chemie., Bd. 441, 1978, Seiten 86-92, XPOO1160738 Verlag Johann Ambrosius Barth. Leipzig., DD ISSN: 0044-2313 * Verbindung der Formel VII *.

* cited by examiner

*Primary Examiner*—Elvis O. Price
(74) *Attorney, Agent, or Firm*—Michael A. Miller

(57) ABSTRACT

The invention relates to a process for synthesizing tertiary phosphines by reacting halophosphines with organomagnesium compounds in the presence of copper compounds and optionally of salts.

17 Claims, No Drawings

PROCESS FOR PREPARING TERTIARY PHOSPHINES

BACKGROUND OF THE INVENTION

1. Field of the Invention

The invention relates to a process for synthesizing tertiary phosphines by reacting halophosphines with organomagnesium compounds in the presence of copper compounds and optionally of salts.

2. Brief Description of the Prior Art

Tertiary phosphines, and methods of using and preparing the same are generally known in the art. Many tertiary phosphines have a high industrial significance, for example as ligands for metal atoms for forming metal complexes, as reducing agents or, in the form of their oxides, as flame retardants or extractants. Metal complexes with tertiary phosphines are frequently used as catalysts in chemical reactions. Tertiary phosphines may also be used for absorbing metals, for example from liquid media.

Tertiary phosphines may typically be synthesized by reacting organometallic compounds with halophosphines. The organometallic compounds used are predominantly organomagnesium and organolithium compounds. However, with increasing steric demands of the organic radicals to be introduced or already present in the molecule, it becomes very difficult to obtain tertiary phosphines. For example, phosphorus trichloride reacts with an excess of tert-butylmagnesium chloride to only give di(tert-butyl)chlorophosphine (see Hoffmann, Schellenbeck, Chemische Berichte, 1967, 100 (2), 692-693), or dichlorophenylphosphine reacts with an excess of tert-butylmagnesium chloride to only give tert-butylchlorophenylphosphine (see Hoffmann, Schellenbeck, Chemische Berichte, 1966, 99, 1134-1142).

In the synthesis of tricyclobexylphosphine from phosphorus trichloride and cyclo-hexylmagnesium compounds, the desired product is obtained only at high temperature and in low yields (see Issleib, Brack; Zeitschr. allg. anorg. Chem. 1954, 277, 258-270).

Stambuli et al. were able to demonstrate that when copper(I) iodide is added in the presence of lithium bromide, it is also possible to use organomagnesium compounds to obtain substitutions on bulky arylalkylchlorophosphines and tert-butylchlorophosphine (J. Am. Chem. Soc., 2001, 123 (11), 2677-2678). The high copper and salt requirements, and likewise the required reaction temperatures of −78° C., make the process industrially impracticable.

Kaye et al. (Adv. Synth. Catal., 2001, 343 (8), 789-794) describes the reaction of bis(aryl Grignard) compounds with chlorophosphines in the presence of copper(I) chloride, requiring large amounts of copper compounds, which complicates the industrial realization.

There was therefore the need to provide a process which makes it possible to synthesize tertiary phosphines in an efficient and industrially acceptable manner.

SUMMARY OF THE INVENTION

A process has now been found for preparing compounds of the formulae (Ia) and (Ib)

$$PR^1{}_nAr_{(3-n)} \quad (Ia)$$

$$R^1{}_2P\text{—}B\text{—}PR^1{}_2 \quad (Ib)$$

where
$R^1$ is in each case $C_1$-$C_{12}$-alkyl, $SiR^2{}_3$, ($C_1$-$C_8$-alkylene)-$SiR^2{}_3$, $C_1$-$C_{12}$-fluoroalkyl, $C_4$-$C_{14}$-aryl or $C_5$-$C_{15}$-arylalkyl where the radicals
$R^2$ are in each case independently $C_1$-$C_{12}$-alkyl and where, in formula (Ia),
n is one, two or three and
Ar is a substituted or unsubstituted aryl radical and where, in formula (Ib),
B is an unsubstituted or substituted radical from the group of $C_1$-$C_{12}$-alkylene, $C_2$-$C_{12}$-alkenylene, $C_4$-$C_{20}$-arylene, $C_8$-$C_{40}$-bisarylene, $C_{10}$-$C_{30}$-ferrocenylene, characterized in that halophosphines of the formula (IIa) or (IIb)

$$PX_nAr_{(3-n)} \quad (IIa)$$

$$X_2P\text{—}B\text{—}PX_2 \quad (IIb)$$

where
n is one, two or three
X is in each case independently chlorine, bromine or iodine and
Ar in formula (IIa) has the same definition as specified under the formula (Ia) and B in formula (IIb) has the same definition as specified under the formula (Ib) are reacted with organomagnesium compounds of the formulae (IIIa)

$$(R^1)_m Mg(Y)_{(2-m)} \quad (IIIa)$$

where
$R^1$ have the definitions specified under the formula (Ia) and
m is one or two and
Y is chlorine, bromine or iodine or halophosphines of the formula (IIc)

$$R^1{}_2PX \quad (IIc)$$

where
$R^1$ has the definition given under the formulae (Ia) and (Ib) are reacted with organomagnesium compounds of the formula (IIIb)

$$B\text{—}(MgY)_2 \quad (IIIb)$$

where
Y is chlorine, bromine or iodine and
where the reaction is in each case carried out
in the presence of one or more copper compounds and
optionally in the presence of salt and
optionally in the presence of solvent.

It is pointed out at this juncture that the scope of the invention also encompasses any desired combinations of areas of preference.

DETAILED DESCRIPTION OF THE INVENTION

In the scope of the invention, Ar is, for example and with preference, a carbocyclic aromatic radical having 6 to 24 framework carbon atoms or a heteroaromatic radical having 4 to 24 framework atoms where no, one, two or three framework atoms per cycle, but at least one framework atom in the entire molecule, are heteroatoms which are selected from the group of nitrogen, sulphur or oxygen. The carbocyclic aromatic radical or heteroaromatic radical may also be substituted by up to five identical or different substituents per cycle which are selected from the group of fluorine, chlorine, bromine, nitro, cyano, protected formyl, $C_1$-$C_{12}$-alkyl, $C_1$-$C_{12}$-fluoroalkyl, $C_4$-$C_{14}$-aryl, $C_5$-$C_{15}$-arylalkyl, —PO—[($C_1$-$C_8$)-alkyl]$_2$, —PO—[($C_4$-$C_{14}$)-aryl]$_2$, —PO—[($C_1$-$C_8$)-alkyl)($C_5$-$C_{14}$)-aryl)], tri($C_1$-$C_8$-alkyl)siloxyl or radicals of the general formula (IV)

$$A-D-R^3 \qquad (IV)$$

where, independently,

A is absent or is a $C_1$-$C_8$-alkylene radical and

D is oxygen, sulphur or $NR^4$ where $R^4$ is hydrogen, $C_1$-$C_8$-alkyl, $C_5$-$C_{15}$-arylalkyl or $C_4$-$C_{14}$-aryl and $R^3$ is $C_1$-$C_8$-alkyl, $C_5$-$C_{15}$-arylalkyl, $C_1$-$C_8$-haloalkyl or $C_4$-$C_{14}$-aryl or $NR^3R^4$ together is a cyclic amino radical or radicals of the general formulae (Va-d)

$$A{-}SOR^3 \qquad (Va)$$

$$A{-}SO_2{-}R^3 \qquad (Vb)$$

$$A{-}CN \qquad (Vc)$$

$$A{-}CO_2M \qquad (Vd)$$

where

A and $R^3$ are each as defined above and M may be an alkali metal ion, half an equivalent of an alkaline earth metal ion or a quaternary ammonium ion.

For the purposes of the invention, alkyl, alkylene, alkoxy, alkenyl and alkenylene are each independently a straight-chain, cyclic, branched or unbranched alkyl, alkylene, alkoxy radical, alkenyl and alkenylene radical respectively, each of which may optionally be further substituted by $C_1$-$C_4$-alkoxy radicals. The same applies to the alkylene moiety of an arylalkyl radical.

$C_1$-$C_4$-alkyl is, for example, methyl, ethyl, n-propyl, isopropyl, n-butyl and tert-butyl, $C_1$-$C_8$-alkyl is additionally n-pentyl, cyclohexyl, n-hexyl, n-heptyl, n-octyl or iso-octyl, $C_1$-$C_{12}$-alkyl is further additionally for example n-decyl and n-dodecyl.

$C_1$-$C_4$-alkylene is, for example, methylene, 1,1-ethylene, 1,2-ethylene, 1,1-propylene, 1,2-propylene, 1,3-propylene, 1,1-butylene, 1,2-butylene, 2,3-butylene and 1,4-butylene, $C_1$-$C_8$-alkylene is additionally 1,5-pentylene, 1,6-hexylene, 1,1-cyclohexylene, 1,4-cyclohexylene, 1,2-cyclohexylene and 1,8-octylene, and $C_1$-$C_{12}$-alkylene is further additionally 1,2-(1,2-dicyclopentyl)ethylene.

$C_2$-$C_{12}$-alkenyl is, for example, ethenyl, allyl, but-3-enyl, hex-5-enyl and dec-10-enyl.

$C_2$-$C_{12}$-alkenylene is, for example, 1,2-ethenylene, 1,4-but-2-enylene, 1,2-cyclopentenylene and 1,2-cyclohexenylene.

$C_1$-$C_4$-alkoxy is, for example, methoxy, ethoxy, isopropoxy, n-propoxy, n-butoxy and tert-butoxy.

The general term aryl as a further substituent encompasses carbocyclic radicals and heteroaromatic radicals in which no, one, two or three framework atoms per cycle, but at least one framework atom in the entire radical, are heteroatoms selected from the group of nitrogen, sulphur or oxygen. $C_4$-$C_{14}$-Aryl is, for example and with preference, phenyl, pyridyl, o-, m-, or p-tolyl, naphthyl or anthracenyl.

The same applies to the aryl moiety of an arylalkyl radical. $C_5$-$C_{15}$-Arylalkyl is, for example and with preference, benzyl.

For the purposes of the invention, fluoroalkyl is in each case independently a straight-chain, cyclic, branched or unbranched alkyl radical which may be singly, multiply or fully substituted by fluorine atoms.

For example and with preference, $C_1$-$C_4$-fluoroalkyl is trifluoromethyl, 2,2,2-trifluoroethyl, pentafluoroethyl and nonafluorobutyl, $C_1$-$C_8$-fluoroalkyl is additionally perfluorocyclohexyl, perfluorohexyl and perfluorooctyl, and $C_1$-$C_{12}$-fluoroalkyl is further additionally perfluorodecyl and perfluorododecyl.

Protected formyl denotes a formyl radical which is protected by conversion to an aminal, acetal or mixed aminalacetal where the aminals, acetals and mixed aminalacetals may be acyclic or cyclic.

For example and with preference, protected formyl is a 1,1-(2,5-dioxy)-cyclopentylene radical.

For the purposes of the invention, Ar is with particular preference a radical selected from the group of phenyl, naphthyl, phenanthrenyl, anthracenyl, fluorenyl, pyridinyl, oxazolyl, thiophenyl, benzofuranyl, benzothiophenyl, dibenzofuranyl, dibenzothiophenyl, furanyl, indolyl, pyridazinyl, pyrazinyl, pyrimidinyl, triazolyl and quinolinyl, each of which may also be substituted by no, one, two or three radicals per cycle, each of which is independently selected from the group of fluorine, chlorine, bromine, nitro, cyano, di($C_1$-$C_6$-alkyl)amino, $C_1$-$C_6$-alkyl, $C_4$-$C_{14}$-aryl, $C_1$-$C_8$-fluoroalkyl, O—($C_1$-$C_{12}$-fluoroalkyl), O—($C_1$-$C_6$-alkyl), —COO—($C_1$-$C_6$)alkyl and —CON($C_1$-$C_6$-alkyl)$_2$.

For the purposes of the invention, Ar is with very particular preference a radical selected from the group of phenyl, naphtyl, phenanthrenyl, anthracenyl and fluorenyl, each of which may also be substituted by no, one, two or three radicals per cycle, each of which is independently selected from the group of fluorine, chlorine, bromine, nitro, cyano, dimethylamino, diethylamino, phenyl, $C_1$-$C_4$-alkyl, $C_1$-$C_4$-fluoroalkyl, O—($C_1$-$C_4$-fluoroalkyl) and O—($C_1$-$C_4$-alkyl).

For the purposes of the invention, B is, for example and with preference, a radical selected from the group of $C_1$-$C_8$-alkylene, $C_2$-$C_{12}$-alkenylene, 1,2-phenylene, 1,3-phenylene, 1,4-phenylene, 1,2-cyclohexylene, 1,1'-ferrocenylene and 1,2-ferrocenylene, each of which may also be mono- or polysubstituted by radicals which are selected from the group of dimethylamino, diethylamino, phenyl, $C_1$-$C_4$-alkyl, bromine, chlorine, fluorine, O—($C_1$-$C_4$-alkyl), S—($C_1$-$C_4$-alkyl), O—($C_1$-$C_4$-fluoroalkyl), CO—O—($C_1$-$C_4$-alkyl), vinyl and allyl.

When B is chiral $C_2$-$C_8$-alkylene or $C_2$-$C_{12}$-alkenylene substituted by the radicals specified, the definition encompasses both pure stereoisomers, enantiomers or diastereomers, and any desired mixtures thereof.

Also for the purposes of the invention, B is, for example and with preference, 1,1'-binaphthyl-2,2'-diyl which is optionally, in each case independently, substituted at the 3,3'-, 4,4'-, 5,5'-, 6,6'-, 7,7'- or 8,8'-positions by radicals which are selected from the group of $C_1$-$C_4$-alkyl, bromine, chlorine, fluorine, O—($C_1$-$C_4$-alkyl), S—($C_1$-$C_4$-alkyl), O—($C_1$-$C_4$-fluoroalkyl), CO—O—($C_1$-$C_4$-alkyl), vinyl and allyl. B is also, for example and with preference, 1,1'-biphenyl-2,2'-diyl which is optionally, in each case independently, substituted at the 3,3'-, 4,4'-, 5,5'- or 6,6'-positions with radicals which are selected from the group of dimethylamino, diethylamino, phenyl, $C_1$-$C_4$-alkyl, bromine, chlorine, fluorine, O—($C_1$-$C_4$-alkyl), S—($C_1$-$C_4$-alkyl), O—($C_1$-$C_4$-fluoroalkyl), CO—O—($C_1$-$C_4$-alkyl), vinyl, allyl, or where in each case two adjacent ring positions (i.e. 3,4; 4,5; 5,6; and/or 3',4'; 4',5'; 5',6') are linked by substituents selected from the group of $C_1$-$C_4$-alkylene, $C_1$-$C_4$-alkylenedioxy, 2-oxyphenyl, 2-thiophenyl, or where the two 6,6'-positions are linked by substituents selected from the group of $C_1$-$C_4$-alkylene, $C_1$-$C_4$-alkylenedioxy, (R)- or (S)-1-alkylethylenedioxy, (R)- or (S)-1-arylethylenedioxy, (R,R)-, (R,S)- or (S,S)-1,2-dialkylethylenedioxy, (R,R)-, (R,S)- or (S,S)-1,2-diarylethylenedioxy, (R,R)-, (R,S)- or (S,S)-1-alkyl-2-arylethylenedioxy.

When racemization-stable atropisomers are observed by the substitution of the biaryl framework, the definition encompasses both the racemates and the pure stereoisomers and also any desired mixtures thereof.

For the purposes of the invention, B is with particular preference 6,6'-dimethoxy-1,1'-biphenyl-2,2'-diyl, 5,5'-dichloro-6,6'-dimethoxy-1,1'-biphenyl-2,2'-diyl, 6,6'-dimethyl-1,1'-biphenyl-2,2'-diyl, 5,5'-dichloro-6,6'-dimethyl-1,1'-biphenyl-2,2'-diyl, 3,3'-di(tert-butyl)-5,5',6,6'-tetramethyl-1,1'-biphenyl-2,2'-diyl, 6,6'-methylenedioxy-1,1'-biphenyl-2,2'-diyl, 6,6'-ethylenedioxy-1,1'-biphenyl-2,2'-diyl, 6,6'-propylenedioxy-1,1'-biphenyl-2,2'-diyl, 6,6'-ethylene-1,1'-biphenyl-2,2'-diyl, 6,6'-propylene-1,1'-biphenyl-2,2'-diyl, 6,6'-butylene-1,1'-biphenyl-2,2'-diyl, 6,6'-[(S)-1-methylethylenedioxy]-1,1'-biphenyl-2,2'-diyl, 6,6'-[(R)-1-methylethylenedioxy]-1,1'-biphenyl-2,2'-diyl, 6,6'-[(S)-1-phenylethylenedioxy]-1,1'-biphenyl-2,2'-diyl, 6,6'-[(R)-1-phenylethylenedioxy]-1,1'-biphenyl-2,2'-diyl, 3,3'-dimethyl-1,1'-binaphthyl-2,2'diyl, 3,3'-dimethoxy-1,1'-binaphthyl-2,2'diyl, 3,3'-di(tert-butyl)-1,1'-binaphthyl-2,2'diyl, 6,6'-dibromo-1,1'-binaphthyl-2,2'diyl, 6,6'-divinyl-1,1'-binaphthyl-2,2'diyl, 6,6'-diallyl-1,1'-binaphthyl-2,2'diyl, bis-4,4'-dibenzofuran-3,3'-diyl, (R)-1-methylethylene-1,2-diyl, (S)-1-methylethylene-1,2-diyl, (R,R)-1,2-dimethylethylene-1,2-diyl, (S,S)-1,2-dimethylethylene-1,2-diyl, (R,R)-1,2-dimethylpropylene-1,3-diyl, (S,S)-1,2-dimethylpropylene-1,3-diyl, (R,R)-1,2-dimethylbutylene-1,4-diyl, (S,S)-1,2-dimethylbutylene-1,4-diyl, (R,R)-1-methyl-2-ethylethylene-1,2-diyl, (S,R)-1-methyl-2-ethylethylene-1,2-diyl, (R,S)-1-methyl-2-ethylethylene-1,2-diyl, (R,R)-1-methyl-2-propylethylene-1,2-diyl, (S,R)-1-methyl-2-propylethylene-1,2-diyl, (R,S)-1-methyl-2-propylethylene-1,2-diyl, (R,R)-1-methyl-2-butylethylene-1,2-diyl, (S,R)-1-methyl-2-butylethylene-1,2-diyl and (R,S)-1-methyl-2-butylethylene-1,2-diyl.

The halophosphines used for the process according to the invention are with particular preference of the formulae (IIa) and (IIb) where
n is equal to two or three.

The halophosphines used for the process according to the invention are also with particular preference those of the formulae (IIa) and (IIb) where
X is chlorine.

The halophosphines used for the process according to the invention are with very particular preference the following compounds:

trichlorophosphine, dichlorophenylphosphine, dichloro-2-methoxyphenylphosphine, dichloro-4-methoxyphenylphosphine, dichloro-2,4-dimethoxyphenylphosphine, dichloro-2,4,6-trimethoxyphenylphosphine, dichloro-2-tolylphosphine, dichloro-4-tolylphosphine, dichloro-2,4-xylylphosphine, dichloro-3,5-xylylphosphine, dichloro-2,4,6-trimethylphenylphosphine, dichloropentafluorophenylphosphine, dichloro-3,5-difluorophenylphosphine, dichloro-2,4-difluorophenylphosphine, dichloro-4-fluorophenylphosphine, dichloro-4-chlorophenylphosphine, dichloro-4-bromophenylphosphine, dichloro-4-(tert-butyl)phenylphosphine, dichloro-2,4,6-tri(tert-butyl)phenylphosphine, dichloro-4-(trifluoromethyl)phenylphosphine, dichloro-3,5-bis(trifluoromethyl)phenylphosphine, dichloro-2-biphenylphosphine, dichloro-3-biphenylphosphine, dichloro-1-naphthylphosphine, dichloro-2-naphthylphosphine, dichloro-5-acenaphthenylphosphine, dichloro-9-fluorenylphosphine, dichloro-9-anthracenylphosphine, dichloro-9-phenanthrylphosphine, dichloro-1-pyrenylphosphine.

For the purposes of the invention, $R^1$ is preferably $C_1$-$C_{12}$-alkyl, $SiR^2_3$, $CH_2SiR^2_3$ or $C_4$-$C_{14}$-aryl where the $R^2$ radicals are in each case independently $C_1$-$C_{12}$-alkyl, although in each case the condition applies that either the $R^1$ radicals are bonded via a secondary, tertiary or quaternary $sp^3$-carbon atom or a quaternary silicon atom and, in the case of bonding via a secondary $sp^3$-carbon atom, this secondary $sp^3$-carbon atom also bears a quaternary $sp^3$-carbon or silicon atom which is likewise a component of the $R^2$ radical or the $R^1$ radicals are $C_4$-$C_{14}$-aryl radicals which are mono- or disubstituted in the ortho-positions.

Such radicals are, for example and with preference, isopropyl, sec-butyl, tert-butyl, trimethylsilyl, 1-methylbutyl, 1-ethylpropyl, 1,1-dimethylpropyl, 1,2-dimethylpropyl, 1-methylpentyl, 1,1-dimethylbutyl, 1,2-dimethylbutyl, 1,3-dimethylbutyl, 1-ethylbutyl, 1,1,2-trimethylpropyl, 1,2,2-trimethylpropyl, 1-ethyl-1-methylpropyl, 2,2-dimethylpropyl, (trimethylsilyl)methyl, cyclopentyl, cyclohexyl and cycloheptyl and also o-tolyl, 2,6-dimethylphenyl, 2,4,6-trimethylphenyl, 2-isopropylphenyl, 2,4- or 2,6-diisopropylphenyl, 2-(tert-butyl) phenyl, 2,4-or 2,6-di(tert-butyl)phenyl or o-anisyl and 2,4- or 2,6-dimethoxyphenyl.

$R^1$ is with particular preference isopropyl, tert-butyl, cyclohexyl, ortho-tolyl and ortho-anisyl, and even greater preference is given to tert-butyl.

Organomagnesium compounds are used for the process according to the invention. Organomagnesium compounds in solution are frequently in equilibrium with their more or less halogen-rich analogues or with solvent- or halogen-bridged di-, oligo- or polymeric structures (known as a Schlenk equilibrium).

The representation of organomagnesium compounds in the form of the formulae (IIIa) and (IIIb), with regard to these equilibria, is not intended to constitute any restriction, but rather merely illustrates organomagnesium compounds in their most frequently reproduced notation.

For the purposes of the invention, organomagnesium compounds, known as Grignard reagents in particular, may, for example, be those which have been prepared in situ from the analogous halogen compounds and magnesium, and the preparation may be effected with the optional use of stoichiometric or catalytic amounts of assistants and additives.

These assistants and additives include further Grignard reagents and alkyl halides such as 1,2-dibromethane, coordinating additives to the solvent such as triethylamine or N,N,N',N'-tetramethyl-1,2-ethylenediamine or metal salts such as iron(II)chloride.

The organomagnesium compounds used may advantageously be used in the form of solutions, some of which are commercially available.

Solvents may also be added to the reaction mixture.

The solvents used are aprotic solvents.

Preferred aprotic solvents are ethers, for example diethyl ether, tert-butyl methyl ether, dioxane, tetrahydrofuran, tetrahydropyran, 1,1-dimethoxymethane, 1,2-dimethoxyethane, diethylene glycol dimethyl ether, tetraethylene glycol dimethyl ether, aliphatic hydrocarbons, for example pentane, hexane, heptane, octane and relatively long-chain unbranched or branched aliphatic hydrocarbons, cyclohexane, methylcyclohexane, petroleum ether having different boiling ranges and paraffin oils, aromatic hydrocarbons, for example benzene, toluene, o-, m- or p-xylene and mesitylene, and aromatic chlorohydrocarbons such as chlorobenzene or the isomeric chlorotoluenes and also mixtures of such solvents.

Particularly preferred solvents are diethyl ether, tetrahydrofuran, toluene, hexane, heptane or mixtures thereof.

In a preferred embodiment of the process according to the invention, the proportion by volume of aromatic or aliphatic hydrocarbons is selected in such a way that, based on the entire reaction mixture, it is 10% or more, preferably 25% or more.

In view of the hydrolysis sensitivity of organomagnesium compounds, the use of dried solvents is advantageous.

In the case of solvents which form a relatively low-boiling azeotrope with water, it has proven sufficient in practice to carry out an azeotropic distillation for drying.

Further drying possibilities are sufficiently well known to those skilled in the art.

The amount of any solvent used may be, for example, 50 ml to 5000 ml, preferably 300 to 1000 ml, per mole of compounds of the general formulae (IIa), (IIb) or (IIc).

The amount of organomagnesium compound used may be, for example, 0.2 to 10 times the molar amount of the halogen atoms to be substituted in the halophosphines of the formulae (IIa), (IIb) or (IIc), and particular preference is given to 0.5 to 5 times, very particular preference to 1 to 2 times. Even greater preference is given to 1.05 to 1.5 times.

The copper compounds used are, for example and with preference, copper salts of the formula (VI)

$$CuAn_q \qquad (VI)$$

where

An is an organic or inorganic monoanion or half an equivalent of an organic or inorganic dianion or copper complexes containing one or more organic ligands which are bonded to the copper atom via one or more atoms from the group of oxygen, nitrogen, sulphur and phosphorus.

Preference is given to using copper salts in anhydrous form. Hydrous copper salts may in principle likewise be used, but it is then advantageous to add an excess of organomagnesium compound, in order to eliminate the water.

Examples of preferred copper salts of the formula (VI) include copper(I) acetate, copper(I) chloride, copper(I) bromide, copper(I) iodide, copper(I) cyanide, copper(I) thiocyanate, copper(II) acetate, copper(II) acetylacetonate, copper (II) chloride, copper(II) bromide, copper(II) ethylhexanoate, copper(II) fluoride, copper(II) formate, copper(II) methoxide, copper(II) nitrate, copper(II) sulphate, copper(II) tartrate, copper(II) trifluoroacetylacetonate and copper(II) trifluoromethanesulphonate, and greater preference is given to copper(I) chloride, copper(I) bromide and copper(I) iodide, and even greater preference is given to copper(I) iodide.

Preferred copper complexes are those which bear ligands which are selected from the group of organic amines and diamines, nitriles, sulphides, phosphines and phosphites.

Examples include 1,2-ethylenediamine, 2,2-bipyridine, 1,10-phenanthroline for amines, acetonitrile and benzonitrile for nitriles, dimethyl sulphide for sulphides, triphenylphosphine for phosphines and trimethyl phosphite for phosphites.

Particularly preferred copper complexes are copper(I) bromide-dimethyl sulphide complex, copper(II) nitrate-1, 10-phenanthroline complex, copper(II) (1,10-phenanthroline) bromide, copper(II) (1,10-phenanthroline) chloride, copper(II) phthalocyanine, copper(I) tetrakis(acetonitrile) hexafluorophosphate, copper(I) (triphenylphosphine) chloride, and even greater preference is given to copper(I) bromide-dimethyl sulphide complex.

For the process according to the invention, very particular preference is given to using copper(I) iodide and copper(I) bromide-dimethyl sulphide complex.

For the process according to the invention, the molar ratio of X to be exchanged in compounds of the formulae (Ia), (Ib) or (Ic) to copper may be, for example, 5 to 2000, although preference is given to a ratio of 10 to 500, very particular preference to one of 50 to 200.

The process according to the invention in a preferred embodiment is carried out in the presence of at least one, preferably one, salt.

The salts used for the process according to the invention are, for example and with preference, salts of the general formula (VII)

$$(cation^+)(anion^-) \qquad (VII)$$

where (cation$^+$) is a substituted ammonium, phosphonium or arsonium cation or an alkali metal ion and (anion$^-$) is the anion of an organic or inorganic acid.

(Cation$^+$) is preferably an alkali metal cation or a cation of the formula (VIII)

$$[Pnic(C_1\text{-}C_{12}\text{-alkyl})_m(C_7\text{-}C_{12}\text{-arylalkyl})_q(C_6\text{-}C_{10}\text{-aryl})_r]^+ \qquad (VIII)$$

where

Pnic is nitrogen or phosphorus and (m+q+r)=4.

(Cation$^+$) is with particular preference lithium, tetraphenylphosphonium, tetrabutylammonium, tetrabutylphosphonium and tributyldodecylphosphonium.

(Anion$^-$) is with preference fluoride, chloride, bromide, iodide, cyanate, thiocyanate, acetate, hydroxide, nitrate, hydrogensulphate, tetrafluoroborate, hexafluorophosphate, tosylate, and triflate, with particular preference chloride, bromide, iodide.

Very particularly preferred salts are tetrabutylphosphonium chloride, tetrabutylphosphonium bromide, tetraphenylphosphonium chloride, tributyldodecylphosphonium chloride, lithium chloride, lithium bromide and lithium iodide or mixtures thereof.

Even greater preference is given to lithium bromide. The molar ratio of salt to copper in the reaction mixture may be, for example, 0.05:1 to 10:1, and preference is given to 0.5:1 to 10:1, particular preference to 1:1 to 4:1.

The reaction temperature may be, for example, −60° C. to 70° C., preferably −20° C. to 70° C. and particularly preferably −10° C. to 50° C.

The reaction pressure is uncritical and may be, for example, 0.2 to 100 bar, preferably ambient pressure.

The reaction time may be, for example, 5 minutes to 24 hours, preferably 30 minutes to 240 minutes.

The reaction and workup are preferably carried out under protective gas with substantial exclusion of oxygen and moisture. Substantial exclusion of oxygen means, for example, a content of oxygen in the protective gas of 1% or less, preferably 0.5% or less. Useful protective gases include, for example, nitrogen and noble gases, for example argon, or mixtures of such gases.

In a preferred embodiment of the process according to the invention, the copper compound and the salt together with the solvent and the halophosphine are initially charged in a reaction vessel under protective gas and the mixture is brought to the reaction temperature with stirring. The organomagnesium compound is then slowly metered in while controlling the reaction temperature. Cooling may optionally be effected. On completion of addition, the reaction mixture is allowed to adjust to room temperature and is stirred until the end of the reaction time. Hydrolysis may then be effected using ammonium chloride solution. After phase separation, the organic phase is washed repeatedly with aqueous ammonia solution and then with water. The organic phase is then dried (for example over MgSO$_4$) and subsequently freed of solvents.

If necessary, sufficiently volatile products are then distilled, while solid products may optionally be further purified, for example by recrystallization or reprecipitation.

An alternative form of workup comprises extraction of the resulting phosphine into the aqueous phase with the aid of inorganic acid and subsequent reextraction into an organic phase after neutralization of the acid with base. The further workup may optionally be effected by distillation or crystallization.

Yet another alternative form of workup comprises the precipitation of the phosphine formed using a strong acid to give a phosphonium salt, in particular those which have negligible solubility in the organic phase. Examples of acids suitable for this purpose include tetrafluoroboric acid, hexafluorophosphoric acid, hexafluorotitanic acid, hexafluorozirconic acid, sulphonic acids, for example tri-fluoromethanesulphonic acid, methanesulphonic acid, toluenesulphonic acid and benzenesulphonic acid, preference is given to tetrafluoroboric acid, hexafluorophosphoric acid, hexafluorotitanic acid and hexafluorozirconic acid, and even greater preference is given to tetrafluoroboric acid and hexafluorophosphoric acid.

The acids specified can also each be used in the form of aqueous solutions.

An aqueous solution of tetrafluoroboric acid is especially suitable. The solid may be isolated and purified. Subsequently, the free phosphine may be obtained by reextraction into an organic phase after neutralization of the acid with base and optionally further purified by distillation or crystallization or the phosphonium salt may be stored or used for further reactions.

Owing to the oxidation sensitivity of phosphines, it is advantageous for all of the liquid media used to be substantially freed of oxygen by degassing.

In the manner according to the invention, phosphines of the formulae (Ia) and (Ib)

$$PR^1{}_nAr_{(3-n)} \qquad (Ia)$$

$$R^1{}_2P-B-PR^1{}_2 \qquad (Ib)$$

are obtained, or the analogous phosphonium tetrafluoroborates, hexafluorophosphates, hydrogen hexafluorozirconates, hydrogen hexafluorotitanates or sulphonates where $R^1$, Ar, n and B each have the definitions and areas of preference described above.

The process according to the invention is suitable in particular for the preparation of aryldialkylphosphines of the general formula (IX)

$$Ar-PR^1{}_2 \qquad (IX)$$

where

Ar has the definition and areas of preference stated under the general formulae (Ia) and (Ib) and $R^1$ has the definition and areas of preference stated under the formulae (Ia) and (Ib), and also for their above-cited phosphonium salts.

The process according to the invention is also suitable in particular for the preparation of trialkylphosphines of the general formula (X)

$$PR^1{}_3 \qquad (X)$$

where $R^1$ has the definition and areas of preference stated under the formulae (Ia) and (Ib), and also for their above-cited phosphonium salts.

The process according to the invention is suitable with particular preference for preparing:
di-(tert-butyl)phenylphosphine, di(1-methylbutyl)phenylphosphine, di(1,1-dimethylpropyl)phenylphosphine, di(1,1-dimethylbutyl)phenylphosphine, di-(tert-butyl)-2-methoxyphenylphosphine, di(1-methylbutyl)-2-methoxyphenylphosphine, di(1,1-dimethylpropyl)-2-methoxyphenylphosphine, di(1,1-dimethylbutyl)-2-methoxyphenylphosphine, bis(trimethylsilyl)-2-methoxyphenylphosphine, di-(tert-butyl)-4-methoxyphenylphosphine, di(1-methylbutyl)-4-methoxyphenylphosphine, di(1,1-dimethylpropyl)-4-methoxyphenylphosphine, di(1,1-dimethylbutyl)-4-methoxyphenylphosphine di-(tert-butyl)-2,4-dimethoxyphenylphosphine, di(1-methylbutyl)-2,4-dimethoxyphenylphosphine, di(1,1-dimethylpropyl)-2,4-dimethoxyphenylphosphine, di(1,1-dimethylbutyl)-2,4-dimethoxyphenylphosphine, di-(tert-butyl)-2,4,6-trimethoxyphenylphosphine, di(1-methylbutyl)-2,4,6-trimethoxyphenylphosphine, di(1,1-dimethylpropyl)-2,4,6-trimethoxyphenylphosphine, di(1,1-dimethylbutyl)-2,4,6-tri-methoxyphenylphosphine, di-(tert-butyl)-2-methylphenylphosphine, di(1-methyl-butyl)-2-methylphenylphosphine, di(1,1-dimethylpropyl)-2-methylphenylphosphine, di(1,1-dimethylbutyl)-2-methylphenylphosphine, di(tert-butyl)-4-methylphenylphosphine, di(1-methylbutyl)-4-methylphenylphosphine, di(1,1-dimethylpropyl)-4-methylphenylphosphine, di(1,1-dimethylbutyl)-4-methylphenylphosphine, di-(tert-butyl)-2,4-dimethylphenylphosphine, di(1-methylbutyl)-2,4-dimethylphenylphosphine, di(1,1-dimethylpropyl)-2,4-dimethylphenylphosphine, di(1,1-dimethylbutyl)-2,4-dimethylphenylphosphine, di-(tert-butyl)-2,4,6-trimethylphenylphosphine, di(1-methylbutyl)-2,4,6-trimethylphenylphosphine, di(1,1-dimethylpropyl)-2,4,6-trimethylphenylphosphine, di(1,1-dimethylbutyl)-2,4,6-tri-methylphenylphosphine, di-(tert-butyl) pentafluorophenylphosphine, di(1-methylbutyl) pentafluorophenylphosphine, di(1,1-dimethylpropyl) pentafluorophenylphosphine, di(1,1-dimethylbutyl) pentafluorophenylphosphine, di-(tert-butyl)-2,4-difluorophenylphosphine, di(1-methylbutyl)-2,4-difluorophenylphosphine, di(1,1-dimethylpropyl)-2,4-difluorophenylphosphine, di(1,1-dimethylbutyl)-2,4-difluorophenylphosphine, di-(tert-butyl)-3,5-difluorophenylphosphine, di(1-methylbutyl)-3,5-difluorophenylphosphine, di(1,1-dimethylpropyl)-3,5-difluorophenylphosphine, di(1,1-dimethylbutyl)-3,5-difluorophenylphosphine, di(tert-butyl)-4-fluorophenylphosphine, di(1-methylbutyl)-4-fluorophenylphosphine, di(1,1-dimethylpropyl)-4-fluorophenylphosphine, di(1,1-dimethylbutyl)-4-fluorophenylphosphine, di(1,2-dimethylbutyl)-4- fluorophenylphosphine, di(tert-butyl)-4-chlorophenylphosphine, di(1-methylbutyl)-4-chlorophenylphosphine, di(1,1-dimethylpropyl)-4-chlorophenylphosphine, di(1,1-dimethylbutyl)-4-chlorophenylphosphine, di(tert-butyl)-4-bromophenylphosphine, di(1-methylbutyl)-4-bromophenylphosphine, di(1,1-dimethylpropyl)-4-bromophenylphosphine, di(1,1-dimethylbutyl)-4-bromophenylphosphine, di(tert-butyl)-4-(tert-butyl)phenylphosphine, di(1-methylbutyl)-4-(tert-butyl)phenylphosphine, di(1,1-dimethylpropyl)-4-(tert-butyl)phenylphosphine, di(1,1-dimethylbutyl)-4-(tert-butyl)phenylphosphine, bis(trimethylsilyl)-4-(tert-butyl)phenylphosphine, di(tert-butyl)-2,4,6-tri(tert-butyl)phenylphosphine, di(1-methylbutyl)-2,4,6-tri(tert-butyl)phenylphosphine, di(1,1-dimethylpropyl)-2,4,6-tri(tert-butyl)phenylphosphine, di(1,1-dimethylbutyl)-2,4,6-tri(tert-butyl)phenylphosphine, di-(tert-butyl)-4-trifluoromethylphenylphosphine, di(1-methylbutyl)-4-trifluoromethylphenylphosphine di(1,1-dimethylpropyl)-4-trifluoromethylphenylphosphine, di(1,1-dimethylbutyl)-4-trifluoromethylphenylphosphine, di-(tert-butyl)-3,5-bis(trifluoromethyl)phenylphosphine, di(1-methylbutyl)-3,5-bis(trifluoromethyl)phenylphosphine, di(1,1-dimethylpropyl)-3,5-bis(trifluoromethyl)phenylphosphine, di(1,1-dimethylbutyl)-3,5-bis(trifluoromethyl)phenylphosphine, di-(tert-butyl)-2-biphenylphosphine, di(1-methylbutyl)-2-biphenylphosphine, di(1,1-dimethylpropyl)-2-biphenylphosphine, di(1,1-dimethylbutyl)-2-biphenylphosphine, di(1,2-dimethylbutyl)-2-biphenylphosphine, bis(trimethylsilyl)-2-biphenylphosphine, di-(tert-butyl)-3-biphenylphosphine, di(1-methylbutyl)-3-biphenylphosphine, di(1,1-dimethylpropyl)-3-biphenylphosphine, di(1,1-dimethylbutyl)-3-biphenylphosphine, di-(tert-butyl)-1-naphthylphosphine, di(1-methylbutyl)-1-naphthylphosphine, di(1,1-dimethylpropyl)-1-naphthylphosphine, di(1,1-dimethylbutyl)-1-naphthylphosphine, di-(tert-butyl)-2-naphthylphosphine, di(1-methylbutyl)-2-naphthylphosphine, di(1,1-dimethylpropyl)-2-naphthylphosphine, di(1,1-dimethylbutyl)-2-naphthylphosphine, di-(tert-butyl)-5-acenaphthylphosphine, di(1-methylbutyl)-5-acenaphthylphosphine, di(1,1-dimethylpropyl)-5-acenaphthylphosphine, di(1,1-dimethylbutyl)-5-acenaphthylphosphine, di-(tert-butyl)-9-fluorenylphosphine, di(1-methylbutyl)-9-fluorenylphosphine, di(1,1-dimethylpropyl)-9-fluorenylphosphine, di(1,1-dimethylbutyl)-9-fluorenylphosphine, di-(tert-butyl)-9-anthracenylphosphine, di(1-methylbutyl)-9-anthracenylphosphine, di(1,1-dimethylpropyl)-9-anthracenylphosphine, di(1,1-dimethylbutyl)-9-anthracenylphosphine, di-(tert-butyl)-9-phenanthrylphosphine, di(1-methylbutyl)-9-phenanthrylphosphine, di(1,1-dimethylpropyl)-9-phenanthrylphosphine, di(1,1-dimethylbutyl)-9-phenanthrylphosphine, di-(tert-butyl)-1-pyrenylphosphine, di(1-methylbutyl)-1-pyrenylphosphine, di(1,1-dimethylpropyl)-1-pyrenylphosphine, di(1,1-dimethylbutyl)-1-pyrenylphosphine, 1,2-bis(di-tert-butylphosphino)benzene, 1,2-, 1,2-bis(di-1-methylbutyl-phosphino)benzene, 1,2-bis[di(1,1-dimethylpropyl)phosphino]benzene, 1,2-bis[bis(1,1-dimethylbutyl)-phosphino]benzene, 1,2-bis[bis(trimethylsilyl)methylphosphino)benzene, 1,3-bis(di-tert-butylphosphino)benzene, 1,3-bis[bis-(trimethylsilylphosphino)]benzene, 1,3-bis(di-1-methylbutylphosphino)benzene, 1,3-bis-[di(1,1-dimethylpropyl)phosphino]benzene, 1,3-bis[bis(1,1-dimethylbutyl)phosphino]benzene, 1,3-bis-[bis(trimethylsilyl)methylphosphino)benzene, 1,4-bis(di-tert-butyl-phosphino)benzene, 1,4-bis(di-1-methylbutylphosphino)benzene, 1,4-bis[di(1,1-dimethylpropyl)phosphino]benzene, 1,4-bis[bis(1,1-dimethylbutyl)phosphino]benzene, 1,4-bis[bis(trimethylsilyl)methylphosphino)benzene. 1,4-bis(di-tert-butyl-phosphino)-cyclohexane, 1,4-bis(di-1-methylbutylphosphino)cyclohexane, 1,4-bis[di(1,1-dimethylpropyl)phosphino]cyclogexane, 1,4-bis[bis(1,1-dimethylbutyl)phosphino]-cyclohexane, 1,4-bis[bis(trimethylsilyl)methylphosphino)cyclohexane, 1,1'-bis(di-tert-butylphosphino)ferrocene, 1,1'-bis(di-1-methylbutylphosphino)ferrocene, 1,1'-bis[di(1,1-dimethylpropyl)phosphino]ferrocene, 1,1'-bis[bis(trimethylsilyl)methylphosphino)ferrocene, 1,2-bis(di-tert-butylphosphino)ferrocene, 1,2-bis(di-1-methylbutylphosphino)ferrocene, 1,2-bis[di(1,1-dimethylpropyl)phosphino]ferrocene, 1,2-bis[bis(1,1-dimethylbutyl)phosphino]ferrocene, 1,2-bis[bis(trimethylsilyl)methylphosphino)ferrocene, tri-tert-butylphosphine, trineopentylphosphine, tris(trimethylsilyl)phosphine, tri(1-methylbutyl)phosphine, tri(1-ethylpropyl)phosphine, tri(1,1-dimethylpropyl)phosphine, tris(1,2-dimethylpropyl)phosphine, tri(1-methylpentyl)phosphine, tris(1,1-dimethylbutyl)phosphine, tris(1,2-dimethylbutyl)phosphine, tris(1,3-dimethylbutyl)phosphine, tri(1-ethylbutyl)phosphine, tris(1,1,2-trimethylpropyl)phosphine, tris(1,2,2-trimethylpropyl)phosphine, tri(1-ethyl-1-methylpropyl)phosphine and tris[(trimethylsilyl)methyl]phosphine, and even greater preference is given to tri(tert-butyl)phosphine, di-tert-butylphosphine and trineopentylphosphine. The process according to the invention is also suitable in particular for preparing di(tert-butyl)phenylphosphonium tetrafluoroborate, di(tert-butyl)phenylphosphonium hexafluorophosphate, di(tert-butyl)phenylphosphonium hydrogenhexafluorozirconate and di(tert-butyl)phenylphosphonium hydrogen hexafluorotitanate. The phosphonium salts mentioned are hitherto unknown and, owing to their outstanding storage stability and the low oxidation sensitivity, they are particularly suitable for use in catalytic processes, in which case the free phosphines are released by adding a base. The phosphonium salts mentioned are therefore likewise encompassed by the invention.

The phosphines which can be prepared according to the invention are suitable for use as ligands in catalytic reactions, in particular in homogeneously transition metal-catalyzed reactions, for example C—C coupling reactions, C—N coupling reactions, C—O coupling reactions, C—S coupling reactions, olefin hydrogenations, olefin hydroformylations, C—C double bond isomerizations, hydrosilylations or allylalkylations. They can also be used for metal-free catalytic reactions, for example the oligomerization of isocyanates.

The phosphines which can be prepared according to the invention are very particularly suitable for catalytic C—C coupling reactions such as the coupling of halogen compounds with organomagnesium, organotin, organozinc or organoboron compounds, olefins or alkines, and also for C—N linkages such as the arylamination, C—S linkages and C—O linkages.

The corresponding phosphonium salts may also advantageously be used in a similar manner to the phosphines when operation is effected with the addition of a base.

This is especially true for di(tert-butyl)phenylphosphonium tetrafluoroborate, di(tert-butyl)phenylphosphonium hexafluorophosphate, di(tert-butyl)phenylphosphonium hydrogen hexafluorozirconate and di(tert-butyl)phenylphosphonium hydrogen hexafluorotitanate.

The advantage of the process according to the invention lies in the simple operation thereof (performability), the high yields and excellent selectivity for tertiary phosphines. The process may also be carried out in aliphatic and aromatic solvents, which is advantageous for an industrial application. In addition, the reaction succeeds at temperatures which can be attained without considerable cost and inconvenience within the scope of an industrial reaction. The process according to the invention is also notable in that it permits excellent yields and selectivity with small amounts of catalyst.

These and other aspects of the invention are further illustrated by the following non-limiting examples.

EXAMPLES

Example 1

Non Inventive

Attempt to prepare di(tert-butyl)phenylphosphine without catalyst in hexane:

In a reaction vessel, 0.4 ml of dichlorophenylphosphine and 3 ml of hexane are initially charged. tert-Butylmagnesium chloride in diethyl ether is then slowly added dropwise with gentle cooling and then stirred at room temperature. After removing the precipitated solid, the course of the reaction is followed by recording a $^{31}$P NMR spectrum. The course of the reaction is illustrated in Table 1.

TABLE 1

| Reaction time [h] | Mol % of ClPPh(tert-butyl) | Mol % of [PPh(t-butyl)]$_2$ | Mol % of PPh(tert-butyl)$_2$ |
|---|---|---|---|
| 1 | 83 | 14 | 1.3 |
| 5 | 49 | 41 | 1.3 |
| 25 | 15 | 71 | 2.1 |

From Table 1, it can be seen that the desired product di(tert-butyl)phenylphosphine is only formed in a very small proportion, while the reactant reacts predominantly to form the undesired 1,2-di(tert-butyl)-1,2-diphenylphosphine.

Example 2

Non Inventive

Attempt to prepare di(tert-butyl)phenylphosphine without catalyst in ether:

In a reaction vessel, 0.4 ml of dichlorophenylphosphine and 3 ml of diethyl ether are initially charged. tert-Butylmagnesium chloride in diethyl ether is then slowly added dropwise with gentle cooling and then stirred at room temperature. After removing the precipitated solid, the course of the reaction is followed by recording a $^{31}$P NMR spectrum. The course of the reaction is illustrated in Table 1.

TABLE 2

| Reaction time [h] | Mol % of ClPPh(tert-butyl) | Mol % of [PPh(t-butyl)]$_2$ | Mol % of PPh(tert-butyl)$_2$ |
|---|---|---|---|
| 1 | 76 | 18 | — |
| 5 | 48 | 41 | 1.5 |
| 25 | 12 | 70 | 2.2 |

From Table 2, it can be seen that the desired product di(tert-butyl)phenylphosphine is only formed in a very small proportion, while the reactant reacts predominantly to form the undesired 1,2-di(tert-butyl)-1,2-diphenylphosphine.

Example 3

Inventive synthesis of di(tert-butyl)phenylphosphine:

5.1 g of copper(I)iodide and 4.6 g of lithium bromide are weighed into a round-bottomed flask equipped with a reflux condenser, thermometer, stirrer and dropping funnel and put under a protective gas atmosphere. 75 ml of hexane are then added, then 36.2 ml of dichlorophenylphosphine are added dropwise. Another 110 ml of hexane are then added and stirred at room temperature for half an hour. The mixture is then cooled to −20° C. and 400 ml of a 2 M tert-butylmagnesium chloride solution in diethyl ether are then added dropwise at such a rate that no noticeable temperature rise occurs. Stirring is then continued at this temperature for one hour, then the mixture is slowly brought to room temperature and stirred for a further two hours. Hydrolysis is then effected using 110 ml of ammonium chloride solution, then the phases are separated and the organic phase is washed three times with conc. ammonia solution, then once with water. The organic phase is then dried over MgSO$_4$ and freed of solvent. The liquid residue is distilled and delivers 41.8 g (71% of theory) of the desired product in a purity of >99.4%.

Examples 4 to 10

Dependence of the reaction upon the catalyst concentration:

In a round-bottomed flask equipped with a stirrer, copper (I)iodide and lithium bromide are weighed in, then put under protective gas, and admixed with hexane solvent and dichlorophenylphosphine. The 2M tert-butylmagnesium chloride solution (in diethyl ether) is then slowly added dropwise at room temperature. Stirring is then continued for 30 minutes and the yield of the tertiary phosphine is determined by recording a $^{31}$P NMR spectrum.

The results with variation of the catalyst concentration are presented in Table 3.

TABLE 3

| Example | Cl$_2$PPh [ml] | Grignard solution [ml] | Hexane [ml] | Cu(I)I [mg] | LiBr [mg] | Cu content[1] [mol %] | Reaction time [min] | Yield [%] |
|---|---|---|---|---|---|---|---|---|
| 4 | 0.3 | 3.31 | 4.5 | 42.1 | 38.4 | 10 | 30 | 94.6 |
| 5 | 0.6 | 6.63 | 9 | 42.1 | 38.4 | 5 | 30 | 94.5 |
| 6 | 1.2 | 13.3 | 18 | 33.7 | 30.7 | 2 | 30 | 91 |
| 7 | 3.0 | 33.2 | 44 | 42.1 | 38.4 | 1 | 30 | 92.3 |
| 8 | 4.5 | 49.7 | 67 | 31.6 | 28.8 | 0.5 | 210 | 61 |

TABLE 3-continued

| Example | Cl$_2$PPh [ml] | Grignard solution [ml] | Hexane [ml] | Cu(I)I [mg] | LiBr [mg] | Cu content[1] [mol %] | Reaction time [min] | Yield [%] |
|---|---|---|---|---|---|---|---|---|
| 9 | 2.71 | 30.0 | 26 | 41.1[2] | 34.7 | 1 | 60 | 88 |
| 10 | 4.07 | 45 | 59 | 31.0[2] | 26.0 | 0.5 | 120 | 90 |

[1]based on the phosphorus content
[2]using copper(I) bromide-dimethyl sulphide complex Examples 11 to 17

Dependence of the reaction upon the temperature:

In a reaction vessel equipped with a stirrer, copper(I) iodide and lithium bromide are weighed in, then put under protective gas, and admixed with hexane solvent and dichlorophenylphosphine. The 2 M tert-butylmagnesium chloride solution (in diethyl ether) is then added dropwise with stirring at the selected temperature at such a rate that there is no distinct increase in the reaction temperature (generally over the course of 20 min). The heating bath is then removed and stirring is continued until the mixtures have attained room temperature once more. Stirring is then continued for a further 1.5 hours and the yield of the tertiary phosphine is determined by recording a $^{31}$P NMR spectrum.

The results with variation of the reaction temperature are presented in Table 4.

TABLE 4

| Example | Cl$_2$PPh [ml] | Grignard solution [ml] | Hexane [ml] | Cu(I)I [mg] | LiBr [mg] | Cu content[1] [mol %] | Temperature [° C.] | Yield [%] |
|---|---|---|---|---|---|---|---|---|
| 11 | 0.275 | 3.0 | 4 | 38.6 | 35.2 | 10 | −40 | 95.6 |
| 12 | 0.275 | 3.0 | 4 | 38.6 | 35.2 | 10 | −20 | 95.8 |
| 13 | 0.275 | 3.0 | 4 | 38.6 | 35.2 | 10 | −10 | 94.8 |
| 14 | 0.275 | 3.0 | 4 | 38.6 | 35.2 | 10 | 0 | 94.9 |
| 15 | 1.35 | 14.9 | 20 | 189.5 | 172.8 | 10 | 50 | 94.3 |
| 16 | 2.71 | 30 | 26 | 0 | 34.7 | 1 | 40 | 6.0 |
| 17 | 2.71 | 30 | 26 | 38.1 | 34.7 | 1 | 40 | 85.9 |

[1]based on the phosphorus content

TABLE 5

| Example | Cl$_2$PPh [ml] | Grignard solution [ml] | Solvent (3 ml) | Cu(I)I [mg] | LiBr [mg] | Yield [%] |
|---|---|---|---|---|---|---|
| 18 | 0.204 | 2.25 | hexane | 29 | 26 | 98.7 |
| 19 | 0.204 | 2.25 | toluene | 29 | 26 | 93.1 |
| 20 | 0.204 | 2.25 | dioxane | 29 | 26 | 91.7 |

Examples 18 to 20

Use of different solvents:

In a reaction vessel equipped with a stirrer, copper(I) iodide and lithium bromide are weighed in, then put under protective gas, and admixed with solvent and dichlorophenylphosphine. The 2M tert-butylmagnesium chloride solution (in diethyl ether) is then added dropwise with stirring at room temperature at such a rate that there remains no possibility of excessive heating. Stirring is then continued for 30 minutes and the yield of the tertiary phosphine is determined by recording a $^{31}$P NMR spectrum.

The results with variation of the solvent are presented in Table 5.

Examples 21 to 24

Dependence of the reaction upon the temperature:

In a round-bottomed flask equipped with a stirrer, copper (I)iodide and lithium bromide are weighed in, then put under protective gas, and admixed with hexane solvent (26 ml) and dichlorophenylphosphine. 30 ml of 2 M tert-butylmagnesium chloride solution (in diethyl ether) are then added dropwise with stirring at the selected temperature at such a rate that there is no noticeable temperature rise. Stirring is then continued for 30 minutes and the yield of the tertiary phosphine is determined by recording a $^{31}$P NMR spectrum.

The results with variation of the temperature are presented in Table 6.

TABLE 6

| Example | Cl₂PPh [ml] | Cu(I)Br · Me₂S [mg] | Cu content[1] [mol %] | LiBr [mg] | Temperature [° C.] | Yield [%] |
|---|---|---|---|---|---|---|
| 21 | 2.71 | 29 | 1 | 34.7 | −40 | 93.2 |
| 22 | 2.71 | 29 | 1 | 34.7 | −20 | 94.3 |
| 23 | 2.71 | 29 | 1 | 34.7 | 0 | 95.0 |
| 24 | 2.71 | 29 | 1 | 34.7 | 40 | 90.4 |

[1]based on the phosphorus content

Example 25

Synthesis of tri(tert-butyl)phosphine:

1.09 g of copper(I)iodide and 1.00 g of lithium bromide are weighed into a flask equipped with a thermometer, reflux condenser and dropping funnel and put under protective gas. 55 ml of hexane, and then 5 ml of phosphorus trichloride are subsequently added and flushing is effected using a further 55 ml of hexane. The mixture is then cooled to −20° C. and 115 ml of 2 M tert-butylmagnesium chloride solution (in diethyl ether) are slowly added dropwise. Stirring is then continued at −20° C. for 1 hour and room temperature for 3 hours.

For workup, hydrolysis is effected using 70 ml of sat. NH₄Cl solution and the organic phase is then removed. This is washed twice with 30 ml each time of conc. ammonia solution and once with water. The organic phase is dried over magnesium sulphate and subsequently concentrated and distilled. 10.23 g yield (88.3% of theory) of colourless liquid which solidifies in the vessel.

Example 26

Synthesis of trineopentylphosphine:

0.70 g of copper(I)iodide and 0.64 g of lithium bromide are weighed into a flask equipped with a thermometer, reflux condenser and dropping funnel and put under protective gas. 50 ml of hexane, and then 3.2 ml of phosphorus trichloride are subsequently added and flushing is effected using a further 25 ml of hexane. The mixture is then cooled to −20° C. and 90 ml of 1.27 M neopentylmagnesium chloride solution (in diethyl ether) are slowly added dropwise. Stirring is then continued at −20° C. for 1 hour and room temperature for 3 hours. The $^{31}$P NMR shows a yield of 75.4% of tri(neopentyl)phosphine.

For workup, hydrolysis is effected using 30 ml of sat. NH₄Cl solution and the organic phase is then removed. This is washed twice with 20 ml each time of conc. ammonia solution and once with water. The organic phase is dried over magnesium sulphate and subsequently concentrated. The remaining oily residue is recrystallized twice from methanol and yields 3.1 g (34.6% of theory) of colourless needles.

Example 27

Synthesis of di(tert-butyl)phenylphosphonium tetrafluoroborate:

In a round-bottomed flask, 60.6 mg of copper(I)bromide-dimethyl sulphide complex and 51.2 mg of lithium bromide are initially charged under protective gas. 20 ml of hexane, 4 ml of dichlorophenylphosphine and another 19 ml of hexane are subsequently added. The reaction solution is cooled to 0° C. 32.4 ml of a 2 M solution of tert-butylmagnesium chloride in ether are then slowly added dropwise. The mixture is subsequently allowed to slowly adjust to room temperature and is then stirred at room temperature for a further two hours. For workup, the mixture is cautiously admixed with 75 ml of degassed 2 M HBF₄. Another 5 ml of 8 M HBF₄ are then additionally added and stirred for 15 min. Filtration with suction is then effected and the filter cake is washed with a little cold water. The residue is dried under reduced pressure to constant weight. Yield: 7.9 g (86% of theory) purity >99%.

$^1$H NMR (CDCl₃, ppm): 7.9 (m, broad); 7.80 (t); 7.69 (2H, td); 6.92 (d, 485 Hz);

1.53 (d, 17 Hz,);

$^{31}$P NMR (CDCl₃, ppm): 44.93 (s)

Example 28

Synthesis of di(tert-butyl)phosphonium hexafluorophosphate:

Similar to Example 27, except that, for workup, the mixture was admixed with 19 ml of degassed 65% hexafluorophosphoric acid which had been diluted to a concentration of 2 M. The mixture is then stirred vigorously for approx. 15 min. Filtration with suction is then effected and the filter cake is washed with a little cold water. The residue is dried under reduced pressure to constant weight. Yield: 8.6 g (79% of theory) purity >99%.

$^1$H NMR (CDCl₃, ppm): 7.9 (m, broad); 7.81 (t); 7.69 (2H, td); 6.807 (d, 483 Hz);

1.53 (d, 17 Hz);

$^{31}$P NMR (CDCl₃, ppm): 45.35 (s); −143.63 (hept., 714 Hz)

Example 29

Synthesis of di(tert-butyl)phosphonium hydrogen hexafluorotitanate:

Similar to Example 27, except that, for workup, the mixture was admixed with 24 ml of degassed 60% hexafluorotitanic acid. The mixture is then stirred vigorously for approx. 15 min, the phases are separated and the aqueous phase is extracted using methylene chloride. The methylene chloride phase is subsequently dried over magnesium sulphate. After distilling off the solvent, the product remains as a colourless residue which is dried under reduced pressure. Yield: 2.4 g, corresponds to 21% of theory.

$^1$H NMR (CDCl₃, ppm): 7.84(m, broad); 7.73 (t, broad); 7.61 (m, broad); 6.85

(d, J=483.5 Hz); 1.46 (d, 17.2 Hz)

$^{31}$P NMR (CDCl₃, ppm): 45.11 (s)

Example 30

Preparation of di(tert-butyl)phosphonium hydrogen hexafluorozirconate:

Similar to Example 27, except that, for workup, the mixture was admixed with 25 ml of degassed 45% hexafluorozirconic acid. The mixture is then stirred vigorously for approx. 15 min, the phases are separated and the aqueous phase is extracted using methylene chloride. The methylene chloride phase is subsequently dried over magnesium sulphate. After distilling off the solvent, the product remains as a colourless residue which is dried under reduced pressure. Yield: 3.67 g, corresponds to 29% of theory.

$^1$H NMR (CDCl$_3$, ppm): 7.82 (m, broad); 7.73 (t, broad); 7.61 (dt), 6.741 (d, J= 387 Hz); 1.46 ppm (d, 17.2 Hz)

$^{31}$P NMR(CDCl$_3$, ppm): 44.979 (s)

Although the invention has been described in detail in the foregoing for the purpose of illustration, it is to be understood that such detail is solely for that purpose and that variations can be made therein by those skilled in the art without departing from the spirit and scope of the invention except as it may be limited by the claims.

What is claimed is:

1. Process for preparing compounds of the formulae (Ia) and (Ib)

$$PR^1{}_nAr_{(3-n)} \quad (Ia)$$

$$R^1{}_2P-B-PR^1{}_2 \quad (Ib)$$

wherein
R$^1$ is in each case C$_1$-C$_{12}$-alkyl, SiR$^2{}_3$, (C$_1$-C$_8$-alkylene)-SiR$^2{}_3$, C$_1$-C$_{12}$-fluoroalkyl, or C$_5$-C$_{15}$-arylalkyl where the radicals
R$^2$ are in each case independently C$_1$-C$_{12}$-alkyl
and wherein, in formula (Ia),
n is one or two and
Ar is a substituted or unsubstituted aryl radical
and wherein, in formula (Ib),
B is an unsubstituted or substituted radical from the group of C$_1$-C$_{12}$-alkylene, C$_2$-C$_{12}$-alkenylene, C$_4$-C$_{20}$-arylene, C$_8$-C$_{40}$-bisarylene, and C$_{10}$-C$_{30}$-ferrocenylene,
comprising: reacting halophosphines of the formulae (IIa) or (IIb)

$$PX_nAr_{(3-n)} \quad (IIa)$$

$$X_2P-B-PX_2 \quad (IIb)$$

wherein
n is one or two and
X is in each case independently chlorine, bromine or iodine and
Ar in formula (IIa) has the same definition as specified under the formula (Ia) and B in formula (IIb) has the same definition as specified under the formula (Ib) with organomagnesium compounds of the formulae (IIIa)

$$(R^1)_mMg(Y)_{(2-m)} \quad (IIIa)$$

wherein
R$^1$ have the definitions specified under the formula (Ia) and
m is one or two and
Y is chlorine, bromine or iodine or
reacting halophosphines of the formula (IIc)

$$R^1{}_2PX \quad (IIc)$$

wherein
R$^1$ has the definition given under the formulae (Ia) and (Ib)
with organomagnesium compounds of the formula (IIIb)

$$B-(MgY)_2 \quad (IIIb)$$

wherein
B has the definition specified under the formula (Ib)
Y is chlorine, bromine or iodine
and
wherein the reaction is in each case carried out in the presence of one or more copper compounds, wherein the tertiary phosphines are precipitated in the form of the analogous phosphonium tetrafluoroborates, hexafluorophosphates, hydrogen hexafluorozirconates, hydrogen hexafluorotitanates or sulphonates by using tetrafluoroboric acid, hexafluorophosphoric acid, hexafluorozirconic acid, hexa-fluorotitanic acid or sulphonic acids.

2. Process according to claim 1, wherein the reaction is carried out in the presence of salt.

3. Process according to claim 2, wherein the salts used are of the formula (VII)

$$(cation^+)(anion^-) \quad (VII)$$

wherein
(cation$^+$) is a substituted ammonium, phosphonium or arsonium cation or an alkali metal ion and
(anion$^-$) is the anion of an organic or inorganic acid.

4. Process according to claim 2, wherein the molar ratio of salt to copper in the reaction mixture is 0.05:1 to 10:1.

5. Process according to claim 1, wherein the reaction is carried out in the presence of solvent.

6. Process according to claim 5, wherein the solvent is selected from the group consisting of aromatic hydrocarbons, aliphatic hydrocarbons, and combinations thereof, wherein the proportion by volume of aromatic or aliphatic hydrocarbons is 10% or more based on the entire reaction mixture.

7. Process according to claim 1, wherein Ar is a carbocyclic aromatic radical having 6 to 24 framework carbon atoms or a heteroaromatic radical having 4 to 24 framework atoms where no, one, two or three framework atoms per cycle, but at least one framework atom in the entire molecule, are heteroatoms which are selected from the group of nitrogen, sulphur or oxygen and where the carbocyclic aromatic radical or heteroaromatic radical is optionally substituted by up to five identical or different substituents per cycle which are selected from the group consisting of fluorine, chlorine, bromine, nitro, cyano, protected formyl, C$_1$-C$_{12}$-alkyl, C$_1$-C$_{12}$-fluoroalkyl, C$_4$-C$_{14}$-aryl, C$_5$-C$_{15}$-arylalkyl, —PO—[(C$_1$-C$_8$)-alkyl]$_2$, —PO—[(C$_5$-C$_{14}$)-aryl]$_2$, —PO—[(C$_1$-C$_8$)-alkyl)(C$_4$-C$_{14}$)-aryl)], tri(C$_1$-C$_8$-alkyl)siloxyl or radicals of the general formula (IV)

$$A-D-R^3 \quad (IV)$$

wherein, independently,
A is absent or is a C$_1$-C$_8$-alkylene radical and
D is oxygen, sulphur or NR$^4$
wherein
R$^4$ is hydrogen, C$_1$-C$_8$-alkyl, C$_5$-C$_{15}$-arylalkyl or C$_4$-C$_{14}$-aryl and
R$^3$ is C$_1$-C$_8$-alkyl, C$_5$-C$_{15}$-arylalkyl, C$_1$-C$_8$-haloalkyl or C$_4$-C$_{14}$-aryl or
NR$^3$R$^4$ together is a cyclic amino radical or radicals of the general formulae (Va-d)

$$A-SOR^3 \quad (Va)$$

$$A-SO_2-R^3 \quad (Vb)$$

$$A-CN \quad (Vc)$$

$$A-CO_2M \quad (Vd)$$

wherein A and $R^3$ are each as defined above and M may be an alkali metal ion, half an equivalent of an alkaline earth metal ion or a quaternary ammonium ion.

8. Process according to claim 1, wherein B is a radical selected from the group of $C_1$-$C_8$-alkylene, $C_2$-$C_{12}$-alkenylene, 1,2-phenylene, 1,3-phenylene, 1,4-phenylene, 1,2-cyclohexylene, 1,1'-ferrocenylene and 1,2-ferrocenylene, each of which is optionally mono- or polysubstituted by radicals which are selected from the group of dimethylamino, diethylamino, phenyl, $C_1$-$C_4$-alkyl, bromine, chlorine, fluorine, O—($C_1$-$C_4$-alkyl), S—($C_1$-$C_4$-alkyl), O—($C_1$-$C_4$-fluoroalkyl), CO—O—($C_1$-$C_4$-alkyl), vinyl and allyl and 1,1'-binaphthyl-2,2'-diyl which is optionally, in each case independently, substituted at the 3,3'-, 4,4'-, 5,5'-, 6,6'-, 7,7'- or 8,8'-positions by radicals which are selected from the group of $C_1$-$C_4$-alkyl, bromine, chlorine, fluorine, O—($C_1$-$C_4$-alkyl), S—($C_1$-$C_4$-alkyl), O—($C_1$-$C_4$-fluoroalkyl), CO—O—($C_1$-$C_4$-alkyl), vinyl and allyl.

9. Process according to claim 1, wherein $R^1$ is $C_1$-$C_{12}$-alkyl, $SiR^2_3$, $CH_2SiR^2_3$ or $C_4$-$C_{14}$-aryl where the $R^2$ radicals are in each case independently $C_1$-$C_{12}$-alkyl, where in each case the condition applies that either the $R^1$ radicals are bonded via a secondary, tertiary or quaternary $sp^3$-carbon atom or a quaternary silicon atom and, in the case of bonding via a secondary $sp^3$-carbon atom, this secondary $sp^3$-carbon atom also bears a quaternary $sp^3$-carbon or silicon atom which is likewise a component of the $R^2$ radical or the $R^1$ radicals are $C_4$-$C_{14}$-aryl radicals which are mono- or disubstituted in the ortho-positions.

10. Process according to claim 1, wherein halophosphines of the formulae (IIa) and (IIb) are used where X is chlorine.

11. Process according to claim 1, wherein the halophosphine used is selected from the group consisting of trichlorophosphine, dichlorophenylphosphine, dichloro-2-methoxyphenylphosphine, dichloro-4-methoxyphenylphosphine, dichloro-2,4-dimethoxyphenylphosphine, dichloro-2,4,6-trimethoxyphenylphosphine, dichloro-2-tolylphosphine, dichloro-4-tolylphosphine, dichloro-2,4-xylylphosphine, dichloro-3,5-xylylphosphine, dichloro-2,4,6-trimethylphenylphosphine, dichloropentafluorophenylphosphine, dichloro-3,5-difluorophenylphosphine, dichloro-2,4-difluorophenylphosphine, dichloro-4-fluorophenylphosphine, dichloro-4-chlorophenylphosphine, dichloro-4-bromophenylphosphine, dichloro-4-(tert-butyl)phenylphosphine, dichloro-2,4,6-tri(tert-butyl)phenylphosphine, dichloro-4-(trifluoromethyl)-phenylphosphine, dichloro-3,5-bis(trifluoromethyl)phenylphosphine, dichloro-2-biphenylphosphine, dichloro-3-biphenylphosphine, dichloro-1-naphthylphosphine, dichloro-2-naphthylphosphine, dichloro-5-acenaphthenylphosphine, dichloro-9-fluorenylphosphine, dichloro-9-anthracenylphosphine, dichloro-9-phenanthrylphosphine, dichloro-1-pyrenylphosphine, and combinations thereof.

12. Process according to claim 1, wherein the amount of organomagnesium compound used is 0.2 to 10 times the molar amount of the halogen atoms to be substituted in the halophosphines of the formulae (IIa), (IIb) or (IIc).

13. Process according to claim 1, wherein the copper compounds used are copper salts of the formula (VI)

$$CuAn_q \qquad (VI)$$

wherein

An is an organic or inorganic monoanion or half an equivalent of an organic or inorganic dianion or copper complexes containing one or more organic ligands which are bonded to the copper atom via one or more atoms from the group of oxygen, nitrogen, sulphur and phosphorus.

14. Process according to claim 1, wherein the copper compounds used are copper(I) iodide and copper(I) bromide dimethyl sulphide complex.

15. Process according to claim 1, wherein the molar ratio of X to be exchanged in compounds of the formulae (IIa), (IIb) or (IIc) to copper is 5 to 2000.

16. Process according to claim 1, wherein the reaction temperature is −60° C. to 70° C.

17. Process according to claim 1, wherein di(tert-butyl) phenylphosphine, is prepared.

* * * * *